US00PP18305P2

(12) United States Plant Patent
Eggleton

(10) Patent No.: US PP18,305 P2
(45) Date of Patent: Dec. 11, 2007

(54) ***LAVANDULA* PLANT NAMED 'BLUEBERRY RUFFLES'**

(50) Latin Name: *Lavandula stoechas*
Varietal Denomination: Blueberry Ruffles

(76) Inventor: Steven Eggleton, 3 Harris Rd., Wonga Park, Melbourne, Vic (AU), 3115

( * ) Notice: Subject to any disclaimer, the term of this patent is extended or adjusted under 35 U.S.C. 154(b) by 35 days.

(21) Appl. No.: 11/435,832

(22) Filed: May 16, 2006

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV ROM GTITM Computer Database 206/04 Citation for 'Blueberry Ruffles'.*

* cited by examiner

*Primary Examiner*—Wendy C. Haas

(57) ABSTRACT

A new cultivar of *Lavandula* plant named 'BLUEBERRY RUFFLES' that is characterized by dense plant habit, early and repeat flowering, large fragrant purple flower spikes with violet-purple medium length sterile bracts. In combination, these traits set 'BLUEBERRY RUFFLES' apart from all other existing varieties of *Lavandula* known to the inventor.

2 Drawing Sheets

Genus: *LAVANDULA.*
Species: *stoechas.*
Denomination: 'BLUEBERRY RUFFLES'.

BACKGROUND OF THE INVENTION

The present invention relates to a new and distinct cultivar of lavender known botanically as *Lavandula stoechas* and hereinafter referred to by the cultivar name 'BLUEBERRY RUFFLES'.

The new *Lavandula* cultivar named 'BLUEBERRY RUFFLES' is one individual selection in the Australian lavender 'Ruffles Series', that resulted from a formal breeding program. The breeding program was established in November 2001 and conducted by the inventor, at the inventor's nursery in Victoria, Australia. The inventor, a specialist in the genus *Lavandula,* selected 'BLUEBERRY RUFFLES' in September 2003. Selection was based on the combination of early and repeat flowering, medium sterile bract length, dense plant habit, short peduncle length, and violet-purple sterile bract color.

'BLUEBERRY RUFFLES' is a selection arising from the controlled cross-pollination of *Lavandula stoechas* 'Kew Red' (unpatented) as the female parent and *Lavandula stoechas* 'Pukehou' (unpatented) as the male parent. Cross-pollination of the parent plants took place in Park Orchards, Victoria, Australia. From this cross the F1 generation was raised in February 2002 and grown to flowering maturity in September 2002. At this stage the F1 generation was self-pollinated and the seed sown in February 2003. From these F2 seedlings a selection was made in September 2003 when the plants had grown to flowering stage in 140 mm. containers.

'BLUEBERRY RUFFLES' is a perennial suitable for use in container or in the landscape. Cultural requirements include full sun, adequate but not excess water, and well-draining soil. Mature height is 60 cm and mature width is 70 cm. 'BLUEBERRY RUFFLES' exhibits early and repeat flowering, dense plant habit, scented green foliage, and large scented purple flower spikes in spring and summer. The sterile bracts are of medium length and violet-purple in color.

The traits that distinguish 'BLUEBERRY RUFFLES' from the female parent 'Kew Red' are sterile bract length and sterile bract color. 'Kew Red' exhibits short pink sterile bracts, whereas 'BLUEBERRY RUFFLES' exhibits violet-purple sterile bracts that are medium length. The traits that distinguish 'BLUEBERRY RUFFLES' from the male parent 'Pukehou' are peduncle length and plant habit. 'Pukehou' exhibits long peduncle length and medium to sparse plant density, compared to 'BLUEBERRY RUFFLES' that exhibits short peduncle length and dense plant habit.

The new *Lavandula* cultivar named, 'BLUEBERRY RUFFLES' was first asexually propagated by the inventor in 2004. Asexual propagation was accomplished at the inventor's nursery in Australia, and the method utilized was tip cuttings. Since that time 'BLUEBERRY RUFFLES' has been determined stable, and reproduces true to type in successive generations of asexual propagation.

SUMMARY OF THE INVENTION

The following traits have been repeatedly observed and represent the distinguishing characteristics of the new *Lavandula* cultivar named 'BLUEBERRY RUFFLES'. These traits in combination distinguish 'BLUEBERRY RUFFLES' from all other existing varieties of *Lavandula* known to the inventor. 'BLUEBERRY RUFFLES' has not been tested under all possible conditions and phenotypic differences may be observed with variations in environmental, climatic, and cultural conditions, without however, any variance in genotype.

1. 'BLUEBERRY RUFFLES' exhibits dense plant habit.
2. 'BLUEBERRY RUFFLES' exhibits large scented purple flower spikes with violet-purple sterile bracts that are medium length.

3. 'BLUEBERRY RUFFLES' exhibits early and repeat flowering.
4. 'BLUEBERRY RUFFLES' is one selection in the Australian lavender 'Ruffles Series' that blooms an average of two weeks earlier than many lavenders in commerce.
5. Cultural requirements for 'BLUEBERRY RUFFLES' are full sun, adequate but not excess water and well-draining soil.
6. 'BLUEBERRY RUFFLES' exhibits short peduncle length.
7. 'BLUEBERRY RUFFLES' is 60 cm in height and 70 cm. in width at maturity.
8. 'BLUEBERRY RUFFLES' is asexually propagated utilizing the method of tip and stem cuttings.
9. 'BLUEBERRY RUFFLES' is suitable for use as an ornamental plant in container or in the landscape.
10. 'BLUEBERRY RUFFLES' is hardy to USDA Zone 8.

BRIEF DESCRIPTION OF THE DRAWINGS

The accompanying drawings illustrate the overall appearance of the new *Lavandula* cultivar named 'BLUEBERRY RUFFLES' showing the colors as true as it is reasonably possible to obtain in color reproductions of this type. Color in the drawings may differ from the color values cited in the detailed botanical description, which accurately describe the actual color of the new *Lavandula* variety named 'BLUEBERRY RUFFLES'. The drawings were made of 9-month-old plants greenhouse grown in 16 cm. containers.

The drawing labeled

The drawing labeled

Figure 1:
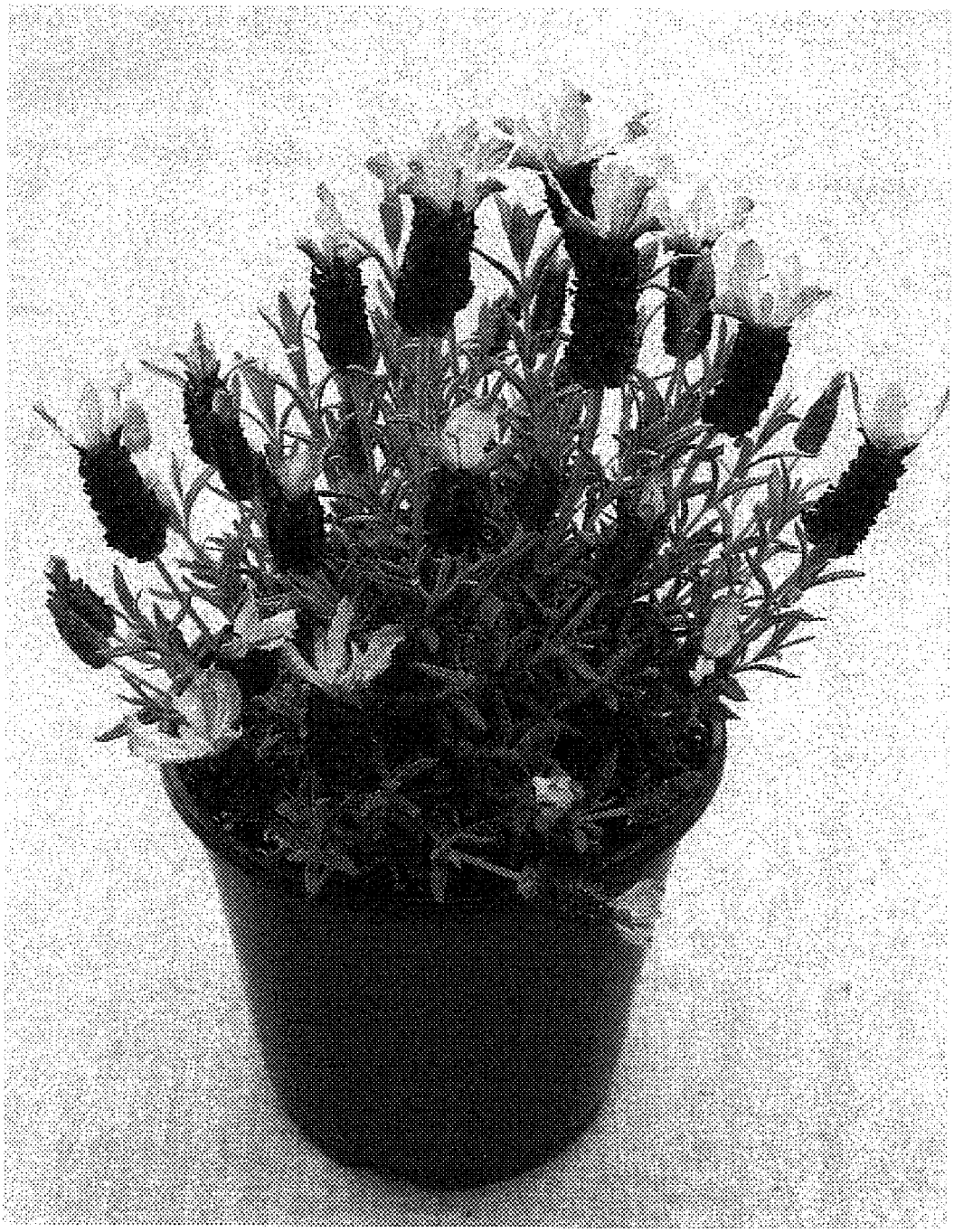
FIG. 1 depicts the plants in bloom from a side perspective.
Figure 2:
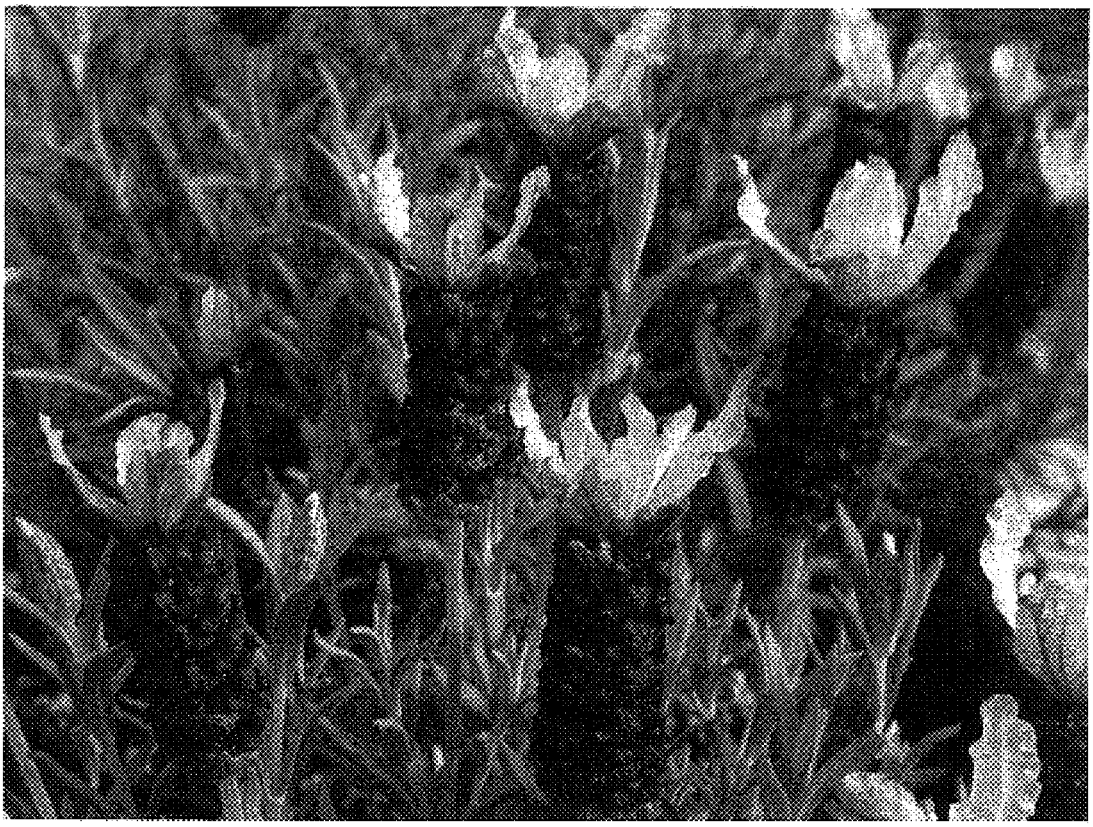
FIG. 2 depicts a close-up view of the flower spike.

Drawings were made using conventional techniques and although the leaf and flower color may appear different from the actual color due to light reflectance, they are as accurate as possible by conventional photography.

BOTANICAL DESCRIPTION OF THE PLANT

The following is a detailed botanical description of the *Lavandula* cultivar named 'BLUEBERRY RUFFLES'. Data was collected in Arroyo Grande, Calif. from 9-month-old plants greenhouse in 16 cm containers. Color determinations are made in accordance with the 2001 Royal Horticultural Society Colour Chart of London, England, except where general color terms of ordinary dictionary significance are used. The growing requirements are similar to the species.

Classification:

*Botanical classification.*—*Lavandula stoechas* 'BLUEBERRY RUFFLES'.
*Family.*—Lamiaceae.
*Genus.*—*Lavandula.*
*Species.*—*Stoechas.*
*Variety denomination.*—'BLUEBERRY RUFFLES'.
*Common name.*—Lavender.

Plant:

*Habit.*—Dense.
*Height* (*at maturity*).—60 cm.
*Width* (*at maturity*).—70 cm.
*Life cycle.*—Perennial.
*Use.*—Ornamental for container or landscape.
*Vigour.*—Moderate.
*Hardiness.*—USDA Zone 8.
*Propagation.*—Tip and stem cuttings.
*Root system.*—Fibrous.
*Cultural requirements.*—Full sun, adequate but not excess water, and well draining soil.
*Time to produce a rooted cutting.*—4–6 weeks.
*Time to produce a* 10 cm container plant in bloom.—20 weeks.
*Seasonal interest.*—Flower spikes in spring and summer.
*Parentage.*—*Lavandula stoechas* 'BLUEBERRY RUFFLES' is a selection that resulted from controlled cross-pollination of the following parents: Female parent plant: *Lavandula stoechas* 'Kew Red'. Male parent plant: *Lavandula stoechas* 'Pukehou'.
*Disease and insect resistance.*—Minimal disease and insect susceptibility, with occasional aphids on new growth.

Stem:

*Branching.*—Erect.
*Stem shape.*—Quadrangular.
*Stem surface.*—Pubescent.
*Pubescence color.*—156D.
*Stem color.*—138B.
*Stem length.*—Average is 8 cm.
*Stem width.*—3 mm.
*Stem fragrance.*—Resinous scent.
*Internode length.*—Average is 1.25 cm.

Foliage:

*Leaf arrangement.*—Opposite.
*Leaf division.*—Simple.
*Leaf shape.*—Linear.
*Leaf margin.*—Entire.
*Leaf apex.*—Acute.
*Leaf base.*—Attenuate.
*Leaf attachment.*—Sessile.
*Leaf color* (*adaxial surface*).—138A.
*Leaf color* (*abaxial surface*).—138B.
*Leaf surface* (*adaxial and abaxial surfaces*).—Tomentose.
*Tomenta color.*—156D.
*Venation.*—Prominent mid-vein observed.
*Vein color* (*adaxial surface*).—138A.
*Vein color* (*abaxial surface*).—138B.
*Leaf length.*—Average is 2.75 cm.
*Leaf width.*—Average is 0.40 cm.
*Leaf fragrance.*—Resinous scent.

Inflorescence:

*Fragrance.*—Resinous scent.
*Blooming period.*—April through August.
*Inflorescence type.*—Spike.
*Spike length.*—5.50 cm.
*Spike diameter.*—3.00 cm.
*Spike shape.*—Cylindrical.
*Spike quantity.*—Range of 30–40.
*Peduncle length.*—6 cm.
*Peduncle width.*—2 mm.
*Peduncle shape.*—Quadrangular.
*Peduncle color.*—138A.
*Peduncle surface.*—Tomentose.
*Tomenta color.*—156D.
*Bud dimensions.*—4 mm in length and 2 mm in width.
*Bud shape.*—Ovoid.
*Bud color.*—N92B.
*Bud surface.*—Lanate.

*Bud apex.*—Acute.

(*Individual flower is referred to as corolla*).—Corolla number: Average of 56 per individual spike. Corolla color: N92A fading to 79A. Corolla shape: Salverform. Corolla depth: 6 mm. Corolla diameter: 2.50 mm. Corolla tube depth: 4 mm. Corolla tube diameter: 1.50 mm. Petals: Four in number. Petals fused or unfused: Basally fused. Petal shape: Reniform. Petal length: 0.75 mm. Petal width: 1.25 mm. Petal apex: Obtuse and emarginated petal apices individually observed on an individual corolla. Petal margin: Entire. Petal surfaces (adaxial and abaxial): Glabrous. Petal color (adaxial and abaxial surfaces): N92A fading to 79A. Calyx color: Individual colors 138B and 79A. Calyx shape: Tubular. Calyx surface: Lanate. Color of hairs: 155B. Calyx length: 4 mm. Calyx width: 2 mm. Sepals: Four in number. Sepals fused or unfused: Fused along three-quarters of the length. Sepal apex: Acute.

(*Fertile bract*).—Fertile bract shape: Deltoid. Quantity: Average of 48 per inflorescence. Fertile bract length: 0.75 cm. Fertile bract width: 0.75 cm. Fertile bract color (ventral and dorsal surfaces): Individual colors N92D and 138B. Vein pattern: Reticulate. Vein color (ventral and dorsal surfaces): N92D. Fertile bract apex: Broadly acute. Fertile bract base: Truncate. Fertile bract surfaces (ventral and dorsal): Lanate. Fertile bract margin: Entire.

(*Sterile bract*).—Sterile bracts: Range of 8–12 per spike. Arrangement: Whorled. Sterile bract appearance: Irridescent. Sterile bract from: Petaloid. Sterile bract surfaces (abaxial and adaxial): Pubescent. Color of hairs: 155B. Sterile bract shape: Oblong-obovate. Sterile bract margin: Combination of sinuous and entire. Sterile bract length: Range of 1.50 cm. to 2.75 cm. Sterile bract width: Range of 0.50 cm. to 1 cm. Sterile bract apex: Rounded. Sterile bract base: Rounded. Sterile bract color (adaxial and abaxial surfaces): 70A or 72A or 72B. Vein pattern: Reticulate. Vein color: N77D.

Reproductive organs:

*Stamens.*—Four in number.

*Stamen form.*—Adnate to ventral surface of corolla tube.

*Stamen color.*—155C.

*Stamen length.*—4 mm.

*Anther.*—Four.

*Anther color.*—163A.

*Pollen color.*—163C.

*Pollen quantity.*—Moderate.

*Pistil.*—One.

*Pistil length.*—3 mm.

*Pistil color.*—155B.

*Stigma height.*—Less than 0.50 mm.

*Stigma surface.*—Glossy.

*Stigma shape.*—Orbicular.

*Stigma color.*—79A.

*Ovary dimensions.*—Less than 0.50 mm.

*Ovary shape.*—Globose.

*Ovary color.*—138A.

*Ovary position.*—Superior.

Seed: No seed has been observed to date.

What is claimed:

1. A new and distinct variety of *Lavandula* plant named 'BLUEBERRY RUFFLES' as described and illustrated herein.

* * * * *